(12) United States Patent
Izawa et al.

(10) Patent No.: US 10,844,030 B2
(45) Date of Patent: Nov. 24, 2020

(54) METHOD FOR PRODUCING FURFURAL

(71) Applicant: Mitsubishi Chemical Corporation, Chiyoda-ku (JP)

(72) Inventors: Yusuke Izawa, Mie (JP); Yosuke Suzuki, Mie (JP); Masaru Utsunomiya, Tokyo (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 16/139,574

(22) Filed: Sep. 24, 2018

(65) Prior Publication Data
US 2019/0023674 A1 Jan. 24, 2019

Related U.S. Application Data

(63) Continuation of application No. PCT/JP2017/012565, filed on Mar. 28, 2017.

(30) Foreign Application Priority Data

Apr. 1, 2016 (JP) .................. 2016-074337

(51) Int. Cl.
C07D 307/50 (2006.01)
(52) U.S. Cl.
CPC ................... C07D 307/50 (2013.01)
(58) Field of Classification Search
CPC .......................................... C07D 307/50
USPC ....................................................... 549/489
See application file for complete search history.

(56) References Cited

U.S. PATENT DOCUMENTS

| 8,524,924 B2 * | 9/2013 | Burket ................. C07D 307/50 549/488 |
| 2016/0076112 A1 | 3/2016 | Cai et al. |
| 2016/0304481 A1 | 10/2016 | Koch et al. |

FOREIGN PATENT DOCUMENTS

| JP | 2012-17325 | 1/2012 |
| WO | WO 2012/115706 A2 | 8/2012 |
| WO | WO 2013/002397 A1 | 1/2013 |
| WO | WO 2015/087248 A1 | 6/2015 |
| WO | WO 2015/126581 A1 | 8/2015 |

OTHER PUBLICATIONS

Dent et al.: Polyphenols from Dalmatian Wild Sage, Food Technol. Biotechnol. 51 (1) 84-91, 2013.*
Collin, Naphthalene and Hydronaphthalenes, Wiley-VCH Verlag GmbH & Co. KGaA, Weinheim, vol. 23, 661-670, 2012.*
Wingard, Journal of the American Oil Chemists' Society vol. 28, pp. 149-152(1951).*
International Search Report dated Jul. 4, 2017 in PCT/JP2017/012565, filed on Mar. 28, 2017 ( with English Translation).
Written Opinion dated Jul. 4, 2017 in PCT/JP2017/012565, filed on Mar. 28, 2017.
Indian Office Action dated Jan. 31, 2020, in Indian Patent Application No. 201817036421.

* cited by examiner

*Primary Examiner* — Nizal S Chandrakumar
(74) *Attorney, Agent, or Firm* — Oblon, McClelland, Maier & Neustadt, L.L.P.

(57) ABSTRACT

The present invention relates to a method for producing furfural, including: obtaining a sugar solution containing at least one of a monosaccharide having 5 carbon atoms and a polysaccharide containing the monosaccharide having 5 carbon atoms by carrying out a reaction with a specific resource as a raw material in the presence of a catalyst in a solvent; converting at least one of the monosaccharide and the polysaccharide containing the monosaccharide in the sugar solution into furfural by a dehydration reaction, so as to obtain a reaction solution; and separating the reaction solution into an organic layer and an aqueous layer, wherein an aromatic hydrocarbon solvent having a density of from 0.90 g/cm$^3$ to 1.1 g/cm$^3$ at 25° C. and under atmospheric pressure is used, and wherein the reaction solution is separated at a temperature higher than 90° C. and lower than 150° C.

14 Claims, No Drawings

METHOD FOR PRODUCING FURFURAL

TECHNICAL FIELD

The present invention relates to a method for producing furfural with a non-edible biomass resource as a raw material.

BACKGROUND ART

Furfural from which a non-edible biomass resource can be obtained can be used as a producing raw material for furfuryl alcohol and tetrahydrofuran, and is a useful compound that can be converted into a polymer producing raw material derived from plants, such as furan resins or PTMG (polytetramethylene ether glycol).

The furfural is produced from the non-edible biomass resource obtaining a sugar solution containing at least one of a monosaccharide (xylose, etc.,) having 5 carbon atoms and a polysaccharide (xylooligosaccharide, etc.,) containing the monosaccharide having 5 carbon atoms as a constituent component by carrying out a reaction on the non-edible biomass resource in the presence of a catalyst in a solvent; hydrolyzing a saccharide in the sugar solution into xylose; and converting the xylulose generated in isomerization of the xylose into furfural by a dehydration reaction, as shown in the following formula. Generally, water is used as a reaction solvent.

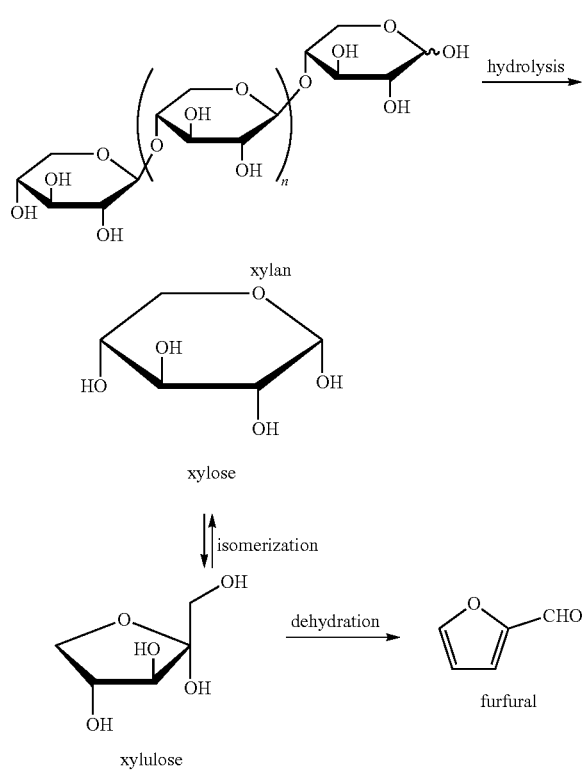

Patent Document 1 describes that, when producing furfural from a lignocellulose raw material, a hydrophobic organic solvent, such as toluene, methyl isobutyl ketone, cyclohexane, and corn oil, together with water is used as a reaction solvent, and a reaction in a two-phase system is carried out.

To recover a reaction solution (hereinafter referred to as "crude furfural" sometimes) containing the furfural generated in the dehydration reaction, the reaction solution containing the furfural is separated into two layers of an organic layer and an aqueous layer, so as to recover the furfural in the organic layer, and the organic layer containing the furfural is further purified by distillation separation or the like, so that the product furfural is obtained.

On the other hand, the separated aqueous layer is recycled to a reaction system. It is because the aqueous layer contains water as the reaction solvent and a catalyst; and also the water and the catalyst can be reused in the reaction system by recycling the aqueous layer.

Accordingly, since the furfural is further purified and separated, and the aqueous layer is recycled and reused, it is desired for the two-layer separation of the dehydration reaction solution to efficiently extract the furfural into the organic layer in a high distribution ratio, and to minimize mixing of organic impurities into the aqueous layer to be recycled and reused.

In addition, the aqueous layer to be recycled and reused is desired to have a high temperature for no increase in heating energy required for the reaction system.

However, generally, in a case of extracting an object into the organic layer by two-layer separation, the extraction efficiency is poor when the temperature is raised. It is common general technical knowledge well known by those skilled in the art that the extraction efficiency at a low temperature is good.

Therefore, in producing the furfural, the temperature condition of two-layer separation of the dehydration reaction solution containing the furfural is preferably low for the aspect of extraction efficiency, and is preferably high for the aspect of recycle and reuse of the aqueous layer, which are contradictory suitable conditions.

BACKGROUND ART DOCUMENT

Patent Document

Patent Document 1: WO 2012/115706

SUMMARY OF THE INVENTION

Problems to be Solved by the Invention

According to the method for producing furfural described in Patent Document 1, the furfural can be recovered in the hydrophobic organic solvent by the two-layer separation; however, it cannot be said that the recovery efficiency and the amount of the organic impurities mixed into the aqueous layer are sufficient.

In addition, Patent Document 1 does not describe the temperature condition of the two-layer separation, nor suggest or describe that the two-layer separation is carried out at a high temperature in order to maintain the temperature of the aqueous layer to be recycled and reused.

The present invention has been made in view of the above problems and an object of the present invention is to provide an industrially advantageous method for producing furfural, in which the furfural can be produced from a non-edible biomass resource by two-layer separation of a dehydration reaction solution at a high temperature into an organic layer containing the furfural and an aqueous layer, so that the furfural can be efficiently extracted into the organic layer in a high distribution ratio, and an aqueous layer having a few amount of organic impurities mixed can be obtained.

Means for Solving the Problem

As a result of an extensive investigation to solve the above problems, the inventors of the present invention have found that, in two-layer separation of the dehydration reaction, the extraction efficiency of the furfural is rapidly improved by carrying out the two-layer separation at a temperature higher than the temperature condition of extraction which is generally considered to be preferable and in a specific temperature range, and selectively using an aromatic hydrocarbon solvent having a specific density range as a solvent to be used for extraction as well, and thus the present invention has been completed. Namely, the gist of the present invention lies in the following [1] to [6].

[1] A method for producing furfural, comprising:
obtaining a sugar solution containing at least one of a monosaccharide having 5 carbon atoms and a polysaccharide containing the monosaccharide having 5 carbon atoms as a constituent component by carrying out a reaction with a non-edible biomass resource as a raw material in the presence of a catalyst in a solvent;
converting at least one of the monosaccharide having 5 carbon atoms and the polysaccharide containing the monosaccharide having 5 carbon atoms as a constituent component in the sugar solution into furfural by a dehydration reaction, so as to obtain a reaction solution containing the furfural; and
two-layer separating the reaction solution into an organic layer containing the furfural and an aqueous layer,
wherein an aromatic hydrocarbon solvent having a density of 0.90 g/cm$^3$ to 1.1 g/cm$^3$ at 25° C. and under atmospheric pressure is used, and
wherein the reaction solution is separated into two layers at a temperature higher than 90° C. and lower than 150° C.

[2] The method for producing furfural according to [1], wherein a concentration of an organic acid in the reaction solution is from 0.1% by weight to 40% by weight.

[3] The method for producing furfural according to [1] or [2], wherein the concentration of the organic acid in the reaction solution is controlled to be from 0.1% by weight to 40% by weight.

[4] The method for producing furfural according to any one of [1] to [3], wherein a boiling point of the aromatic hydrocarbon solvent is from 160° C. to 280° C. under atmospheric pressure.

[5] The method for producing furfural according to any one of [1] to [4], wherein a concentration of acetic acid in the reaction solution is from 0.2% by weight to 2% by weight.

[6] A method for producing furfural, comprising:
obtaining a sugar solution containing at least one of a monosaccharide having 5 carbon atoms and a polysaccharide containing the monosaccharide having 5 carbon atoms as a constituent component by carrying out a reaction with a non-edible biomass resource as a raw material in the presence of a catalyst in a solvent;
converting at least one of the monosaccharide having 5 carbon atoms and the polysaccharide containing the monosaccharide having 5 carbon atoms as a constituent component in the sugar solution into furfural by a dehydration reaction, so as to obtain a reaction solution containing the furfural; and
separating the reaction solution into two layers of an organic layer containing the furfural and an aqueous layer, and obtaining the furfural continuously,
wherein an aromatic hydrocarbon solvent having a density of from 0.90 g/cm$^3$ to 1.1 g/cm$^3$ at 25° C. and under atmospheric pressure is used, and
wherein the reaction solution is separated into two layers at a temperature higher than 90° C. and lower than 150° C.

Effect of the Invention

According to the present invention, when producing the furfural from the non-edible biomass resource, by carrying out two-layer separation of the dehydration reaction solution, the furfural can be efficiently extracted into the organic layer in a high distribution ratio, and the aqueous layer including a few amount of mixed organic impurities can be obtained.

Therefore, while the purified furfural can be obtained from the separated organic layer in high yield, the amount of the organic impurities which are contained in the aqueous layer to be recycled and reused; and which are incorporated in the reaction system can be reduced to prevent accumulation of contamination substances in the reaction system, so that reduction of maintenance and improvement of reaction efficiency can be achieved.

Moreover, in the present invention, since the two-layer separation is carried out at a temperature higher than a conventional extraction temperature of a solution containing furfural, such as higher than 90° C. and lower than 150° C., the temperature of the aqueous layer to be to be recycled and reused in the reaction system can be maintained high and the heating energy required for the reaction system can be reduced. In addition, since the organic layer also has a high temperature, the heating energy can be reduced in the next step such as distillation separation.

Mode For Carrying Out Invention

Although the embodiments of the present invention will be described in detail hereinafter, the present invention is not limited to the following embodiments, and can be implemented by various modifications within the scope of the present invention.

A method for producing furfural of the present invention is characterized by: obtaining a sugar solution containing at least one of a monosaccharide having 5 carbon atoms and a polysaccharide containing a monosaccharide having 5 carbon atoms as a constituent component (hereinafter may be referred to as a "C5 saccharide") by carrying out a reaction with a non-edible biomass resource as a raw material in the presence of a catalyst in a solvent; converting the C5 saccharide in the sugar solution into furfural by a dehydration reaction, so as to obtain a reaction solution containing the furfural; and carrying out two-layer separation of the reaction solution into an organic layer containing the furfural and an aqueous layer, wherein an aromatic hydrocarbon solvent having a density of from 0.90 g/cm$^3$ to 1.1 g/cm$^3$ at 25° C. and under atmospheric pressure is used, and the reaction solution is separated into two layers at a temperature higher than 90° C. and lower than 150° C.

The method for producing furfural from the non-edible biomass resource includes a producing step of obtaining the sugar solution containing the C5 saccharide from the non-edible biomass resource and a producing step of obtaining the furfural by the dehydration reaction of the C5 saccharide in the sugar solution. However, in the present invention, the producing step of the sugar solution and the producing step of the furfural may be carried out in one reactor, or may be carried out in separate reactors.

In addition, in the present invention, the dehydration reaction solution is separated into two layers of the organic layer containing the furfural and the aqueous layer. Herein, an organic solvent constituting the organic layer may be one that is already present in the reaction solution as a reaction solvent, or may be an organic solvent that is added as an extraction solvent to the obtained reaction solution after the dehydration reaction, or may be both the organic solvent contained in the dehydration reaction solution and the organic solvent added after the dehydration reaction.

<Non-Edible Biomass Resource>

The non-edible biomass resource used in the present invention is not particularly limited as long as it contains a polysaccharide with a saccharide as a constituent component. Specifically, examples include bagasse, switchgrass, napier grass, erianthus, miscanthus, kenaf, corn stover, corn cobs, beet pulp, palm fruit bunches, rice straws, wheat straws, rice bran, trees, woods, vegetable oil residue, sasa, bamboos, pulps, waste paper, food waste, fishery residues, livestock discarding, or the like. In addition, waste molasses left after recovery of sugar from molasses generated at a producing step of the sugar can also be used as the non-edible biomass resource. Of these, from the viewpoint of availability of the raw material and the cost, bagasse, corn stover, corn cobs, and rice straws are preferable, bagasse and corn cobs are more preferable, and bagasse is particularly preferable. Unlike the edible biomass resource, the non-edible biomass resource does not compete with food applications. Since there are usually many resources to be subjected to waste incineration treatment, it is preferable from the viewpoint of achieving stable supply and effective use of resources.

These non-edible biomass resources can be used as they are, or can be used after pre-treatment such as acid treatment and hydrothermal treatment. In addition, these non-edible biomass resources may be used alone or may be used in combination of two or more thereof. Further, these non-edible biomass resources may be supplied to the reactor in a solid state, or may be supplied in a state of slurry mixed with a solvent such as water.

From the viewpoint of handleability and reaction efficiency, it is preferable that the non-edible biomass resources have a weight average diameter of 0.5 mm or more, more preferably 1 mm or more, and particularly preferably 2 mm or more, as a length of a longest part of a particle. In addition, it is preferable that the weight average diameter is 50 mm or less, more preferably 25 mm or less, and particularly preferably 10 mm or less.

The weight average diameter of the non-edible biomass resources can be measured by a sieving method using a sieve (manufactured by IIDA SEISAKUSHO CO., LTD) having a mesh size of 10 mm, 4.76 mm, 2.0 mm, 1.0 mm, 0.5 mm, and 0.42 mm, for example.

<C5 Saccharide>

The C5 saccharide to be used in the present invention is derived from a non-edible biomass resource, or may be one from which furfural can be produced by a dehydration reaction, and is not particularly limited.

Specific examples of a monosaccharide having 5 carbon atoms (pentose) include ribose, lyxose, xylose, arabinose, deoxyribose, xylulose, ribulose, or the like. These monosaccharides are abundant because they are natural constituent components of plants, and from the viewpoint of the availability of the raw material and the yield, xylose and arabinose are preferable, and xylose is more preferable.

Specific examples of a polysaccharide, having the above monosaccharide having 5 carbon atoms as a constituent component, include disaccharides such as xylobiose and arabinobiose, trisaccharides such as xylotriose and arabinotriose, oligosaccharides such as xylooligosaccharides and arabinoligosaccharides including the above disaccharides and trisaccharides, polysaccharides such as xylan, araban, and hemicellulose, or the like. Of these polysaccharides, from the viewpoint of the yield, xylooligosaccharide, xylan, and hemicellulose are preferable, and among which xylooligosaccharide is particularly preferable. Herein, the xylooligosaccharide is one containing the disaccharide and the trisaccharide as main components, and further containing tetrose to hexose.

The sugar solution obtained from the non-edible biomass resource may contain only one of the monosaccharide and polysaccharide, or may contain two or more thereof. In addition, monosaccharides such as glucose and polysaccharides such as glucan which are different in the number of carbon atoms from the C5 saccharide may coexist in the sugar solution.

<Reaction for Producing Sugar Solution>

The reaction for producing a sugar solution containing the above C5 saccharide from the non-edible biomass resource is a reaction to hydrolyze a hemicellulose component in the non-edible biomass resource to produce a C5 saccharide. From the viewpoint of improving the productivity of the C5 saccharide and improving the purity of the obtained C5 saccharide, this reaction is carried out with using a reaction solvent and a catalyst.

Hereinafter, the reaction for producing a sugar solution is described.

(Concentration of Non-Edible Biomass Resource)

In the reaction for producing a sugar solution from the non-edible biomass resource, the concentration of the non-edible biomass resource contained in the reaction solvent is not particularly limited. However, it is preferable that a proportion of the non-edible biomass resource to the solvent is from 0.1% by weight to 200% by weight, more preferably from 5% by weight to 40% by weight, and still more preferably from 10% by weight to 30% by weight. When the proportion of the non-edible biomass resource to the solvent is equal to or larger than the above lower limit value, the energy required for solvent separation tends to be lower, and further the capacity of the reaction system tends to be reduced and thus the construction cost of equipment tends to possibly reduced. When the proportion of the non-edible biomass resource to the solvent is equal to or less than the above upper limit value, the side reaction can be prevented, and the yields of the C5 saccharide and the furfural tend to increase, which is preferable.

(Catalyst)

The catalyst to be used in the reaction for producing a sugar solution from the non-edible biomass resource is not particularly limited as long as it is a catalyst capable of producing the C5 saccharide from the non-edible biomass resource. Examples of an acid catalyst include inorganic acids such as sulfuric acid, phosphoric acid, nitric acid and hydrochloric acid, organic acids such as carboxylic acids and sulfonic acids, heteropoly acids, or the like. Of these, from the viewpoint of stability, corrosivity, waste disposal, and unit price, the organic acids are preferable, and the carboxylic acids are particularly preferable.

Specific examples of the carboxylic acids include: aliphatic carboxylic acids such as formic acid, acetic acid, propionic acid, butyric acid, pentanoic acid, hexanoic acid, heptanoic acid, octanoic acid, nonanoic acid, decanoic acid, dodecanoic acid, tetradecanoic acid, levulinic acid and lactic acid; aliphatic dicarboxylic acids such as oxalic acid, malonic acid, succinic acid, glutaric acid, adipic acid, pimelic acid, suberic acid, azelaic acid, sebacic acid, aconitic acid, itaconic acid, oxaloacetic acid, fumaric acid, cis-1,2-cyclopentanedicarboxylic acid, trans-1,2-cyclopentanedicarboxylic acid, cis-1,3-cyclopentanedicarboxylic acid, trans-1,3-cyclopentanedicarboxylic acid, cis-1,2-cyclohexanedicarboxylic acid, trans-1,2-cyclohexanedicarboxylic acid, cis-1,3-cyclohexanedicarboxylic acid, trans-1,3-cyclohexanedicarboxylic acid, cis-1,4-cyclohexanedicarboxylic acid, and trans-1,4-cyclohexanedicarboxylic acid; aliphatic tricarboxylic acids such as 1,2,4-cyclohexanetricarboxylic acid, and 1,3,5-cyclohexanetricarboxylic acid; aromatic carboxylic acids such as benzoic acid, and naphthalenecarboxylic acid; aromatic polycarboxylic acids such as phthalic acid, isophthalic acid, terephthalic acid, trimesic acid, trimellitic acid, hemimellitic acid, melophanic acid, prenitic acid, pyromellitic acid, benzene pentacarboxylic acid, and mellitic acid; heterocyclic carboxylic acids such as furancarboxylic acid, and furandicarboxylic acid; or the like. In addition, salts neutralizing at least a part of these acids can also be used.

Of these, formic acid, acetic acid, lactic acid, and levulinic acid, which are acids obtained from the non-edible biomass resource, are preferable.

In particular, from the viewpoint of the yield of the C5 saccharide, among the above carboxylic acids, the acid dissociation constant pKa is preferably from 1 to 5, and particularly preferably from 3.0 to 4.6. Herein, the acid dissociation constant pKa refers to a numerical value in a case where the dissociation stage is 1. Namely, it means, in a case of carboxylic acid having two or more carboxyl groups, an acid dissociation constant pKa in a case where at least one hydrogen ion of two or more carboxyl groups is desorbed. For example, in succinic acid having two carboxyl groups, usually the pKa is 4.19 for dissociation stage 1 and 5.48 for dissociation stage 2, but in the present specification, 4.19 for dissociation stage 1 is defined as the pKa of the succinic acid.

The above carboxylic acids can be used alone, or may be used in combination of two or more thereof.

Specific examples of the sulfonic acids include methanesulfonic acid, ethanesulfonic acid, propanesulfonic acid, butanesulfonic acid, pentanesulfonic acid, hexanesulfonic acid, benzenesulfonic acid, toluenesulfonic acid, naphthalenesulfonic acid, or the like. In addition, salts neutralizing at least a part of these acids can also be used.

The above sulfonic acids can be used alone, or may be used in combination of two or more thereof.

Specific examples of the heteropoly acids include phosphotungstic acid, silicotungstic acid, phosphomolybdic acid, silicomolybdic acid, phosphovanadomolybdic acid, silicovanadomolybdic acid, or the like. In addition, salts neutralizing at least a part of these acids can also be used.

The above heteropoly acids can be used alone, or may be used in combination of two or more thereof.

In addition, the above carboxylic acids, sulfonic acids and heteropoly acids may be used by mixing two or more thereof in any ratio. Further, it is preferable to separate the catalyst in the process and recycle the catalyst.

An amount of the catalyst to be used in the reaction for producing a sugar solution can be appropriately set according to the type of the catalyst and reaction conditions, and is not particularly limited. However, it is preferable that the amount of the catalyst is from 0.01% by weight to 50% by weight, more preferably from 0.5% by weight to 30% by weight, and particularly preferably from 1% by weight to 20% by weight, based on an amount of the solution. Herein, the "solution" refers to a reaction solution containing a reaction solvent, a non-edible biomass resource and a catalyst, which are described later. When the amount of the catalyst is equal to or larger than the above lower limit value, the reaction rate tends to increase and the productivity of the C5 saccharide tends to be improved. When the amount of the catalyst is equal to or less than the above upper limit value, it is preferable since the side reaction can be prevented and the selectivity of the C5 saccharide tends to be improved, which is preferable.

(Reaction Solvent)

The reaction solvent to be used in the reaction for producing a sugar solution from the non-edible biomass resource is water, or a mixed solvent of water and an organic solvent. Namely, the reaction can be carried out with using water only, or the reaction can be carried out by adding an organic solvent. In a case of using an organic layer, the reaction can be carried out with using a homogeneous mixed solvent, or an organic solvent which is a two-layer system of an aqueous layer and an organic layer can also be used. An amount of the organic solvent to be used is not particularly limited as long as the gist of the present invention is not impaired. However, it is preferable that the amount of the organic solvent is from 10% by weight to 5000% by weight, and particularly preferably from 10% by weight to 1000% by weight, based on the water.

The above organic solvent is not particularly limited. Examples include: ethers having 4 to 20 carbon atoms such as tetrahydrofuran; alcohols having 3 to 20 carbon atoms such as 1-propanol and 2-propanol; saturated aliphatic hydrocarbons having 3 to 12 carbon atoms such as pentane, hexane, cyclohexane, heptane, octane, nonane, decane, dodecane, and isododecane; aromatic hydrocarbons such as toluene, xylene, diethylbenzene, trimethylbenzene, 1,2,3,4-tetrahydronaphthalene (tetralin), and 1-methylnaphthalene; lactones such as γ-butyrolactone and γ-valerolactone; glycols such as polyethylene glycol; glycol ethers such as polyethylene glycol dimethyl ether; in addition, sulfolane, isosorbide, isosorbide dimethyl ether, propylene carbonate; or the like.

Of these, an aqueous solvent to be a homogeneous mixed solvent with water or a nonpolar solvent which is hardly soluble in the above-mentioned acid catalyst is preferable. Among these, the aromatic hydrocarbon solvents such as toluene, xylene, diethylbenzene, trimethylbenzene, 1,2,3,4-tetrahydronaphthalene (tetralin), and 1-methylnaphthalene are particularly preferable as organic solvents suitable for two-layer separation in a case of carrying out a reaction in a two-layer system, since they are organic solvents constituting an organic layer of the two-layer separation, from the viewpoint of extraction efficiency of furfural and reduction of dissolved amount of the organic solvent in water. Of these, as a solvent with good extraction efficiency of furfural, a solvent having a value $(\gamma^\infty_{FRL}/\gamma^\infty_{H_2O})$, obtained by dividing an infinite dilution activity coefficient (described as "$\gamma^\infty_{FRL}$") of the furfural in a solvent by an infinite dilution activity coefficient (described as "$\gamma^\infty_{H_2O}$") of water in the solvent, of 3 or more is preferable, particularly preferably a solvent having a value $(\gamma^\infty_{FRL}/\gamma^\infty_{H_2O})$ of 10 or more, and most preferably a solvent having a value $(\gamma^\infty_{FRL}/\gamma^\infty_{H_2O})$ of 15 or more.

Although it is preferable that the above organic solvent is a single solvent considering the recovery and reuse of the solvent, two or more kinds may be used.

In the present invention, since the two-layer separation is carried out at a higher temperature higher than 90° C. and lower than 150° C., it is preferable to use the aromatic hydrocarbon solvent as an organic solvent to be an organic solvent constituting an organic layer in two-layer separation, which has a density approximate to the density of water at normal temperature (25° C.) and under atmospheric pressure (100 kPa), has a density greatly different from the density of water at a temperature higher than 90° C. and lower than 150° C., and has high temperature dependency of density, as described below.

In addition, from the viewpoint of separating and purifying furfural from the organic layer containing the furfural by distillation separation, one having a high boiling point as a high boiling side is preferable in the distillation separation.

From the above viewpoint, it is preferable that the aromatic hydrocarbon solvent to be used in the present invention has a density, at normal temperature (25° C.) and under atmospheric pressure (100 kPa), of from 0.90 g/cm$^3$ to 1.10 g/cm$^3$, and particularly of from 0.95 g/cm$^3$ to 1.05 g/cm$^3$, approximate to the density of water. In addition, as for the temperature dependency of density, it is preferable that the density has a high temperature dependency such that the density at normal temperature (25° C.) and under atmospheric pressure (100 kPa) is within the above range, and the density is from 0.6 g/cm$^3$ to 0.99 g/cm$^3$, and particularly from 0.7 g/cm$^3$ to 0.95 g/cm$^3$, at a temperature higher than 90° C. and lower than 150° C. and under atmospheric pressure (100 kPa).

Further, as for the boiling point of the aromatic hydrocarbon solvent to be used in the present invention, it is preferable that the boiling point is from 160° C. to 280° C., and it is more preferably from 165° C. to 250° C., which is sufficiently higher than the boiling point (161.7° C.) of furfural, under atmospheric pressure (100 kPa).

In the present invention, as the aromatic hydrocarbon solvent satisfying the above density and boiling point, the following solvents are preferably used: tetralin (having a density at normal temperature (25° C.) and under atmospheric pressure (100 kPa) of 0.970 g/cm$^3$, and a density at 100° C. and under atmospheric pressure (100 kPa) of 0.905 g/cm$^3$, and having a boiling point under atmospheric pressure (100 kPa) of from 206° C. to 208° C.), 1-methylnaphthalene (having a density at normal temperature (25° C.) and under atmospheric pressure (100 kPa) of 1.001 g/cm$^3$, and a density at 100° C. and under atmospheric pressure (100 kPa) of 0.961 g/cm$^3$, and having a boiling point under atmospheric pressure (100 kPa) of from 240° C. to 243° C.), indane (having a density at normal temperature (25° C.) and under atmospheric pressure (100 kPa) of 0.965 g/cm$^3$, and a density at 100° C. and under atmospheric pressure (100 kPa) of 0.894 g/cm$^3$, and having a boiling point under atmospheric pressure (100 kPa) of 177° C.), cyclohexylbenzene (having a density at normal temperature (25° C.) and under atmospheric pressure (100 kPa) of 0.939 g/cm$^3$, and a density at 100° C. and under atmospheric pressure (100 kPa) of 0.878 g/cm$^3$, and having a boiling point under atmospheric pressure (100 kPa) of 236° C.), aniline (having a density at normal temperature (25° C.) and under atmospheric pressure (100 kPa) of 1.021 g/cm$^3$, and a density at 100° C. and under atmospheric pressure (100 kPa) of 0.954 g/cm$^3$, and having a boiling point under atmospheric pressure (100 kPa) of 184° C.), acetophenone (having a density at normal temperature (25° C.) and under atmospheric pressure (100 kPa) of 1.027 g/cm$^3$, and a density at 100° C. and under atmospheric pressure (100 kPa) of 0.958 g/cm$^3$, and having a boiling point under atmospheric pressure (100 kPa) of 202° C.), m-cresol (having a density at normal temperature (25° C.) and under atmospheric pressure (100 kPa) of 1.034 g/cm$^3$, and a density at 100° C. and under atmospheric pressure (100 kPa) of 0.971 g/cm$^3$, and having a boiling point under atmospheric pressure (100 kPa) of 202° C.), benzaldehyde (having a density at normal temperature (25° C.) and under atmospheric pressure (100 kPa) of 1.046 g/cm$^3$, and a density at 100° C. and under atmospheric pressure (100 kPa) of 0.973 g/cm$^3$, and having a boiling point under atmospheric pressure (100 kPa) of 178° C.), benzyl alcohol (having a density at normal temperature (25° C.) and under atmospheric pressure (100 kPa) of 1.046 g/cm$^3$, and a density at 100° C. and under atmospheric pressure (100 kPa) of 0.981 g/cm$^3$, and having a boiling point under atmospheric pressure (100 kPa) of 205° C.), and ethyl benzoate (having a density at normal temperature (25° C.) and under atmospheric pressure (100 kPa) of 1.048 g/cm$^3$, and a density at 100° C. and under atmospheric pressure (100 kPa) of 0.971 g/cm$^3$, and having a boiling point under atmospheric pressure (100 kPa) of 213° C.), and tetralin is particularly preferably used.

(Reaction Condition)

The reaction temperature of the reaction for producing a sugar solution is not particularly limited. Specifically, 100° C. or higher is preferable; 120° C. or higher is more preferable; and 160° C. or higher is still more preferable; 250° C. or lower is preferable, and 230° C. or lower is more preferable. When the reaction temperature is equal to or higher than the above lower limit value, the reaction tends to progress fast and the productivity for producing the C5 saccharide is improved. When the reaction temperature is equal to or lower than the above upper limit value, it is preferable since the sequential reaction and decomposition of the C5 saccharide tend to be prevented and the yield of the C5 saccharide tends to be increased.

The heating method is not particularly limited. A method of raising the temperature of the reaction solution with a heat exchanger, a method of directly introducing steam into the reaction solution, a method of heating with using liquid in a high temperature process by recycling the separated solvent after the reaction, or the like are preferable. From the viewpoint of using the heat energy efficiently, the method of heating with using liquid in a high temperature process is particularly preferable.

The reaction time of the reaction for producing a sugar solution varies depending on the amount and kind of the raw material and catalyst used, and the reaction temperature. Specifically, 0.02 hour or more is preferable; 0.1 hour or more is more preferable; and 0.2 hour or more is particularly preferable, and 5 hours or less is preferable; 2 hours or less is more preferable; and 1 hour or less is particularly preferable. When the reaction time is equal to or longer than the above lower limit value, progress of the reaction tends to be promoted and the yield of the C5 saccharide tends to be improved. When the reaction time is equal to or shorter than the above upper limit value, it is preferable since the decomposition and sequential reaction of the C5 saccharide tends to be prevented and the yield of the C5 saccharide tends to be improved.

The preferable range of the reaction pressure varies depending on the reaction temperature; 0.1 MPaG to 5.0 MPaG is preferable, 0.5 MPaG to 3.0 MPaG is more preferable, and 1.0 MPaG to 2.5 MPaG is particularly preferable.

(Reaction Type)

The reaction type of the reaction for producing a sugar solution is not particularly limited, and may be a batch type, a semi-batch type or a continuous type, or a reaction type combining the above. Herein, the continuous type refers to a reaction of continuous removal of the obtained sugar solution by continuously supplying a non-edible biomass resource as a raw material and reacting them. In addition, from the viewpoint of solid-liquid contact, a rotary reactor is preferable. The reactor may have one unit or a plurality of series of units may be combined.

(Solid-Liquid Separation)

After the reaction for producing a sugar solution, a solid-liquid separation method for separating solid reaction residues of the non-edible biomass resource from the reaction solution is not particularly limited. It is preferably to use a filter press, a belt filter, a screw press, a roll press, a conveyor dryer, an Oliver filter, a pre-coat filter, a disc filter, a belt press, a Gina centrifugal separator, a rotary pressure dehydration device, a multiple disc dehydration device, a hollow fiber membrane filtration device, a cross flow type centrifugal filtration dehydration device, or the like; more preferably a filter press, a belt filter, a roll press; and particularly preferably a roll press. The solid-liquid separation may be carried out after producing the sugar solution, or may be carried out after producing the furfural by the dehydration reaction, or may be carried out during the production of the sugar solution or the furfural.

<Reaction for Producing Furfural>

The reaction for producing furfural carried out in the present invention is a reaction for producing furfural by carrying out a dehydration reaction of the C5 saccharide in the sugar solution obtained by the above reaction for producing a sugar solution, in the presence of a catalyst. From the viewpoint of improving the productivity of the furfural and improving the purity of the obtained furfural, it is preferable that this dehydration reaction is carried out with using a reaction solvent and a catalyst. In addition, the above reaction for producing furfural can not be separated from the above reaction for producing a sugar solution, and the furfural can be directly obtained from bagasse under the conditions described in the reaction for producing a sugar solution.

(Concentration of C5 Saccharide of Sugar Solution)

As described above, the concentration of C5 saccharide of sugar solution which is produced from the non-edible biomass resource and supplied to the dehydration reaction for producing furfural is not particularly limited. However, it is preferable that a proportion of the C5 saccharide to the sugar solution is from 0.1% by weight to 50% by weight, more preferably from 1% by weight to 30% by weight, and still more preferably from 4% by weight to 10% by weight. When the content of the C5 saccharide in the sugar solution is equal to or larger than the above lower limit value, after the dehydration reaction, the energy required for separating the furfural and the solvent tends to be lower, and further the capacity of the reaction system tends to be reduced and thus the construction cost can be reduced. When the concentration of the C5 saccharide in the sugar solution is equal to or less than the above upper limit value, the side reaction can be prevented, and the yield of the furfural tends to increase, which is preferable.

(Catalyst)

The catalyst to be used in the reaction for producing furfural of the present invention is not particularly limited as long as it is a catalyst capable of producing the C5 saccharide from the furfural. Those similar to the catalyst used in the above reaction for producing a sugar solution from the non-edible biomass resource can be used. The preferable catalyst is also similar to those used in the above reaction for producing a sugar solution from the non-edible biomass resource.

An amount of the catalyst to be used in the reaction for producing furfural can be appropriately set according to the type of the catalyst and reaction conditions, and is not particularly limited. However, it is preferable that the amount of the catalyst is from 0.01% by weight to 50% by weight, more preferably from 0.5% by weight to 30% by weight, and particularly preferably from 1% by weight to 20% by weight, based on an amount of the solution. Herein, the "solution" refers to a reaction solution containing a reaction solvent, a C5 saccharide and a catalyst, which are described later. When the amount of the catalyst is equal to or larger than the above lower limit value, the reaction rate tends to increase and the productivity of the furfural tends to be improved. In addition, since the furfural has a polymerizing property under acidic conditions, when the amount of the catalyst is equal to or less than the above upper limit value, the side reaction tends to be prevented and the selectivity of the furfural tends to be improved, which is preferable.

(Reaction Solvent)

It is preferable that the reaction solvent to be used in the reaction for producing furfural is water, or a mixed solvent of water and an organic solvent. Namely, similar to the reaction for producing a sugar solution from the non-edible biomass resource, the reaction can be carried out with using water only, or the reaction can be carried out by adding an organic solvent. From the viewpoint of cost advantage, it is preferable to only use water as the reaction solvent. From the viewpoint of improving the yield of the furfural, it is preferable to use water and an organic solvent as the reaction solvent.

The reaction can be carried out with using a homogeneous mixed solvent by adding an organic solvent. However, in order to prevent the polymerization or decomposition reaction of the furfural and to improve the yield of the furfural, it is preferable to use an organic solvent which is a two-layer system of an aqueous layer and an organic layer. An amount of the organic solvent to be used is not particularly limited as long as the gist of the present invention is not impaired. However, it is preferable that the amount of the organic solvent is from 10% by weight to 5000% by weight, and particularly preferably from 10% by weight to 1000% by weight, based on the water.

The organic solvent to be used is not particularly limited. Any of the above organic solvents as the organic solvent used in the reaction for producing a sugar solution from the non-edible biomass resource can be used. The suitable organic solvent is also similar to those have be described.

Also in the reaction for producing furfural, although it is preferable that the above organic solvent is a single solvent considering the recovery and reuse of the solvent, two or more kinds may be used.

(Reaction Condition)

The reaction temperature of the reaction for producing furfural is not particularly limited. Specifically, 100° C. or higher is preferable; 120° C. or higher is more preferable; and 160° C. or higher is still more preferable; and 250° C. or lower is preferable, and 230° C. or lower is more preferable. When the reaction temperature is equal to or higher than the above lower limit value, the reaction rate tends to increase and the productivity of the furfural is improved. When the reaction temperature is equal to or lower than the above upper limit value, it is preferable since the decomposition and polymerization of the furfural and the raw material saccharide tend to be prevented and the yield of the furfural tends to be improved.

The reaction time of the reaction for producing furfural varies depending on the composition of the sugar solution, the amount and kind of the catalyst used, and the reaction temperature. Specifically, 0.02 hour or more is preferable; 0.1 hour or more is more preferable; and 0.5 hour or more is particularly preferable; and 5 hours or less is preferable, and 2 hours or less is more preferable. When the reaction time is equal to or larger than the above lower limit value, progress of the reaction tends to be promoted, and the yield of the furfural tends to be improved since the conversion rate is increased. When the reaction time is equal to or shorter than the above upper limit value, it is preferable since the decomposition or polymerization of the furfural tends to be prevented and the yield of the furfural tends to be improved.

The preferable range of the reaction pressure varies depending on the reaction temperature; 0.1 MPaG to 5.0 MPaG is preferable; 0.5 MPaG to 3.0 MPaG is more preferable; and 1.0 MPaG to 2.5 MPaG is particularly preferable.

(Reaction Type)

The reaction type of the reaction for producing furfural is not particularly limited, and may be a batch type, a semi-batch type or a continuous type, or a reaction type combining the above. However, from the viewpoint of improving the productivity, the semi-batch type reaction or the continuous type reaction are preferable. The continuous type reaction herein refers to a reaction in which the above sugar solution as a raw material for obtaining furfural is continuously supplied and reacted, and the reaction solution containing the obtained furfural is continuously extracted. In the continuous type reaction, a continuous tubular reactor or a continuous tank reactor can be used. In addition, a reactive distillation method may be used in which distillation is carried out with producing the furfural as a reaction product. For example, as described in International Publication WO 2013/102027, a method for continuously extracting a mixture of furfural and water by using a reactor for producing furfural as a reactive distillation type, and as described in International Publication WO 2012/115706, a method for continuously extracting furfural from an aqueous layer with using an organic solvent can also be used. In the case of the reactive distillation method, the method may be carried out under reduced pressure or at normal pressure. The reactor may have one unit or a plurality of series of units may be combined.

<Two-Layer Separation>

In the present invention, as described above, the reaction solution (crude furfural) containing the furfural obtained by the dehydration reaction of the C5 saccharide in the sugar solution is separated into two layers of an organic layer containing the furfural and an aqueous layer.

As described below, the two-layer separation can be carried out by a routine procedure with using a two-layer separator such as a regular decanter, in addition that the temperature condition and the concentration of the organic acid in the organic layer are controlled.

(Concentration of Furfural in Crude Furfural)

The concentration of the furfural in the crude furfural for two-layer separation is not particularly limited. It is generally from 0.01% by weight to 10% by weight; preferably from 0.1% by weight to 8% by weight; more preferably from 0.5% by weight to 6% by weight; and most preferably from 1% by weight to 5% by weight. When the concentration of the furfural in the crude furfural is equal to or larger than the above lower limit value, the extraction efficiency of the furfural is improved, and the amount of the solvent for the furfural is lowered and thus the production cost can be reduced. When the concentration of the furfural in the crude furfural is equal to or less than the above upper limit value, it is preferable since polymers derived from the furfural can be reduced.

The concentration of the furfural in the crude furfural can be controlled by the amount of the reaction solvent used, the reaction temperature, the reaction pressure, the reaction time, the stirring speed, the type of the catalyst, the amount of the catalyst, the concentration of the non-edible biomass resource, the particle diameter of the non-edible biomass resource, the type of the non-edible biomass resource, or the like.

(Concentration of Organic Acid in Crude Furfural)

The crude furfural contains an organic acid used as a catalyst for producing furfural, and an organic acid such as acetic acid and formic acid generated in the dehydration reaction.

In the present invention, it is preferable that the concentration of the organic acid in the crude furfural is from 0.1% by weight to 40% by weight. In addition, it is more preferable that the concentration of the organic acid in the crude furfural is from 0.5% by weight to 30% by weight; from 1% by weight to 20% by weight is particularly preferable; and from 1.5% by weight to 5% by weight is especially preferable.

When the concentration of the organic acid in the crude furfural is equal to or larger than the above lower limit value, the productivity of the furfural can be improved with using a sufficient amount of the organic acid as a catalyst, and the density of the aqueous layer is increased and thus the distribution efficiency to the organic layer of the furfural is enhanced. When the concentration of the organic acid in the crude furfural is equal to or less than the above upper limit value, the distribution ratio to the organic layer of the furfural tends to be enhanced, the cost for separating the organic acid tends to be lowered and polymerization of the furfural tends to be prevented.

Therefore, it is preferable to control the concentration of the organic acid in the crude furfural within the above ranges. In order to carry out the control, for example, it is preferable to use an organic acid as a catalyst; to adjust the condition of generating acetic acid and formic acid from a non-edible biomass resource; and to purge the organic acid or recycle an organic acid containing solution in the process.

(Concentration of Acetic Acid in Crude Furfural)

The crude furfural generally contains acetic acid, which is generated in the reaction for producing a sugar solution and the dehydration reaction of the C5 saccharide, or used as a catalyst.

In the present invention, it is preferable that the concentration of the acetic acid in the crude furfural is from 0.2% by weight to 10% by weight; from 0.4% by weight to 5% by weight is particularly preferable; and from 0.6% by weight to 3% by weight is especially preferable.

When the concentration of the acetic acid in the crude furfural is equal to or larger than the above lower limit value, the density of the aqueous layer is increased and thus the distribution efficiency to the organic layer of the furfural is enhanced. When the concentration of the acetic acid in the crude furfural is equal to or less than the above upper limit value, the cost for separating the acetic acid tends to be lowered and polymerization of the furfural tends to be prevented.

Therefore, in order to control the concentration of the acetic acid in the crude furfural within the above ranges, it is preferable to adjust the condition of generating the acetic acid from a non-edible biomass resource; to use the acetic acid as a catalyst; and to purge the acetic acid or recycle an acetic acid containing solution in the process.

(Concentration of Formic Acid in Crude Furfural)

The crude furfural generally contains formic acid, which is generated in the reaction for producing a sugar solution and the dehydration reaction of the C5 saccharide.

In the present invention, it is preferable that the concentration of the formic acid in the crude furfural is from 0.05% by weight to 5% by weight, particularly preferably from 0.1% by weight to 2% by weight, and especially preferably from 0.15% by weight to 1% by weight.

When the concentration of the formic acid in the crude furfural is equal to or larger than the above lower limit value, the density of the aqueous layer is increased and thus the distribution efficiency to the organic layer of the furfural is enhanced. When the concentration of the formic acid in the crude furfural is equal to or less than the above upper limit value, the cost for separating the formic acid tends to be lowered and polymerization of the furfural tends to be prevented.

Therefore, in order to control the concentration of the formic acid in the crude furfural within the above ranges, it is preferable to adjust the condition of generating the formic acid from a non-edible biomass resource, to use the formic acid as a catalyst, and to purge the formic acid or recycle a formic acid containing solution in the process.

(Extraction Solvent)

As described above, from the viewpoint of the extraction efficiency of the furfural and a reduced dissolved amount of the organic solvent in water, the aromatic hydrocarbon solvent to be used in extracting the furfural by two-layer separation is particularly preferably toluene, xylene, diethylbenzene, 1,2,4-trimethylbenzene, 1,2,3,4-tetrahydronaphthalene (tetralin), 1-methylnaphthalene, indane, cyclohexylbenzene, cymene, or the like. Of these, as a solvent with good extraction efficiency of furfural, a solvent having a value ($\gamma^\infty_{FRL}/\gamma^\infty_{H2O}$), obtained by dividing an infinite dilution activity coefficient ($\gamma^\infty_{FRL}$) of the furfural in a solvent by an infinite dilution activity coefficient ($\gamma^\infty_{H2O}$) of water in the solvent, of 3 or more is preferable, particularly preferably a solvent having a value ($\gamma^\infty_{FRL}/\gamma^\infty_{H2O}$) of 10 or more, and most preferably a solvent having a value ($\gamma^\infty_{FRL}/\gamma^\infty_{H2O}$) of 15 or more.

As described above, it is preferable that the aromatic hydrocarbon solvent to be used in the present invention has a density, at normal temperature (25° C.) and under atmospheric pressure (100 kPa), of from 0.90 g/cm$^3$ to 1.10 g/cm$^3$, and particularly of from 0.95 g/cm$^3$ to 1.05 g/cm$^3$, approximate to the density of water. In addition, it is preferable that the density has a high temperature dependency such that the density is from 0.6 g/cm$^3$ to 0.99 g/cm$^3$, and particularly from 0.7 g/cm$^3$ to 0.95 g/cm$^3$ at a temperature higher than 90° C. and lower than 150° C. and under atmospheric pressure (100 kPa).

In addition, the solvent having a boiling point of from 160° C. to 280° C., and particularly from 165° C. to 250° C. under atmospheric pressure (100 kPa) is preferable, and the followings are used as such a solvent: tetralin (having a density at normal temperature (25° C.) and under atmospheric pressure (100 kPa) of 0.970 g/cm$^3$, and a density at 100° C. and under atmospheric pressure (100 kPa) of 0.905 g/cm$^3$, and having a boiling point under atmospheric pressure (100 kPa) of from 206° C. to 208° C.), 1-methylnaphthalene (having a density at normal temperature (25° C.) and under atmospheric pressure (100 kPa) of 1.001 g/cm$^3$, and a density at 100° C. and under atmospheric pressure (100 kPa) of 0.961 g/cm$^3$, and having a boiling point under atmospheric pressure (100 kPa) of from 240° C. to 243° C.), indane (having a density at normal temperature (25° C.) and under atmospheric pressure (100 kPa) of 0.965 g/cm$^3$, and a density at 100° C. and under atmospheric pressure (100 kPa) of 0.894 g/cm$^3$, and having a boiling point under atmospheric pressure (100 kPa) of 177° C.), cyclohexylbenzene (having a density at normal temperature (25° C.) and under atmospheric pressure (100 kPa) of 0.939 g/cm$^3$, and a density at 100° C. and under atmospheric pressure (100 kPa) of 0.878 g/cm$^3$, and having a boiling point under atmospheric pressure (100 kPa) of 236° C.), aniline (having a density at normal temperature (25° C.) and under atmospheric pressure (100 kPa) of 1.021 g/cm$^3$, and a density at 100° C. and under atmospheric pressure (100 kPa) of 0.954 g/cm$^3$, and having a boiling point under atmospheric pressure (100 kPa) of 184° C.), acetophenone (having a density at normal temperature (25° C.) and under atmospheric pressure (100 kPa) of 1.027 g/cm$^3$, and a density at 100° C. and under atmospheric pressure (100 kPa) of 0.958 g/cm$^3$, and having a boiling point under atmospheric pressure (100 kPa) of 202° C.), m-cresol (having a density at normal temperature (25° C.) and under atmospheric pressure (100 kPa) of 1.034 g/cm$^3$, and a density at 100° C. and under atmospheric pressure (100 kPa) of 0.971 g/cm$^3$, and having a boiling point under atmospheric pressure (100 kPa) of 202° C.), benzaldehyde (having a density at normal temperature (25° C.) and under atmospheric pressure (100 kPa) of 1.046 g/cm$^3$, and a density at 100° C. and under atmospheric pressure (100 kPa) of 0.973 g/cm$^3$, and having a boiling point under atmospheric pressure (100 kPa) of 178° C.), benzyl alcohol (having a density at normal temperature (25° C.) and under atmospheric pressure (100 kPa) of 1.046 g/cm$^3$, and a density at 100° C. and under atmospheric pressure (100 kPa) of 0.981 g/cm$^3$, and having a boiling point under atmospheric pressure (100 kPa) of 205° C.), and ethyl benzoate (having a density at normal temperature (25° C.) and under atmospheric pressure (100 kPa) of 1.048 g/cm$^3$, and a density at 100° C. and under atmospheric pressure (100 kPa) of 0.971 g/cm$^3$, and having a boiling point under atmospheric pressure (100 kPa) of 213° C.), and tetralin is particularly preferably used.

It is preferable that the amount of the extraction solvent used is from 10% by weight to 1000% by weight, particularly from 20% by weight to 700% by weight, and especially from 50% by weight to 150% by weight, based on the crude furfural. In addition, it is preferable that the amount of the extraction solvent used is from 300% by weight to 30000% by weight, particularly from 600% by weight to 20000% by weight, and especially from 1200% by weight to 5000% by weight, based on the furfural in the crude furfural.

When the amount of the extraction solvent used is equal to or larger than the above lower limit value, the extraction efficiency of the furfural tends to be enhanced and the concentration of impurities in the aqueous layer tends to be lowered. When the amount of the extraction solvent used is equal to or less than the above upper limit value, the amount of the solvent used and loss in solvent during the whole process can be reduced, and the construction cost of equipment can be reduced.

Therefore, in a case where the amount of the organic solvent contained in the dehydration reaction solution is less than the above lower limit value, it is preferable to compensate for shortage by adding the organic solvent at carrying out the two-layer separation. Generally, the amount of the organic solvent in the dehydration reaction solution hardly exceeds the above upper limit value. However, in a case where the amount of the organic solvent in the dehydration reaction solution exceeds the above upper limit value, the amount of the solvent newly supplied to the process may be reduced, or a part of the solvent recovered from a distillation column for recovering a solvent may be extracted out of the system.

(Temperature of Two-Layer Separation)

The present invention is characterized by carrying out the two-layer separation at a temperature higher than 90° C. and lower than 150° C. By making the temperature of the two-layer separation higher than 90° C., the temperature of the separated aqueous layer is sufficiently high, which is suitable for recycle and reuse, and the separation efficiency of the furfural can be improved and loss in solvent to water can be reduced. On the other hand, by making the temperature of the two-layer separation lower than 150° C., the furfural can be effectively recovered by preventing the polymerization of the furfural, and the amount of the solvent or impurities mixed into the aqueous layer can be reduced. From such a viewpoint, it is preferable that the temperature of the two-layer separation is from 95° C. to 140° C., and more preferably from 100° C. to 130° C.

(Separation Time)

The separation time required for the two-layer separation in the present invention, for example, a standing time in a two-layer separator such as a decanter, varies depending on the separation temperature, the amount of the extraction solvent or the like. Generally, the separation time is 5 minutes or more, preferably 10 minutes or more, more preferably 15 minutes or more, and particularly preferably 20 minutes or more; and generally 4 hours or less, preferably 3 hours or less, more preferably 2 hours or less, and particularly preferably 1 hour or less. When the separation time is longer than the above upper limit value, a long decanter is required and the polymerization reaction of the furfural or impurities is increased, which is not preferable. When the separation time is shorter than the above lower limit value, the separation efficiency of the furfural tends to deteriorate and loss in solvent tends to increase, which is not preferable. According to the present invention, the furfural can be extracted and separated efficiently even in a short separation time.

<Concentration and Distribution Ratio of Furfural in Organic Layer>

In the present invention, it is preferable that, in the above two-layer separation, an organic layer having a concentration of furfural of from 0.5% by weight to 5% by weight can be obtained with a distribution ratio of furfural of from 60% to 99%.

Herein, the distribution ratio of furfural refers to a proportion (percentage) of the amount of the furfural extracted into the organic layer with respect to the total amount of the furfural contained in the crude furfural supplied for the two-layer separation.

EXAMPLES

Hereinafter, although the present invention is described in more detail by way of examples, but the present invention is not limited to the following Examples unless it goes beyond the gist thereof.

In the following Examples, moisture analysis was carried out with using a Karl Fischer method (measured by CA-21 manufactured by Mitsubishi Chemical Corporation). Analyses on furfural, acetic acid, and lactic acid of the crude furfural, furfural in the organic layer and aqueous layer, and the organic solvent in the aqueous layer were carried out by gas chromatography (GC), and were calculated by an internal standard method. In addition, 1,4-dioxane was used in the internal standard.

The formic acid in the crude furfural was analyzed by capillary electrophoresis under the following conditions.

Capillary electrophoresis apparatus: "CAPI-3300 Type" manufactured by Otsuka Electronics Co., Ltd.

A sample was diluted in ultrapure water or an aqueous solution of isopropanol, and the formic acid in the diluent was measured by the capillary electrophoresis.

Based on the above CG analysis result, the yield of furfural (FRL) was determined according to the following calculation formula. In this connection, for xylan, as a unit of $(C_5H_8O_4)_n$, xylan (1 mol) formed by bonding n of xylose was regarded as n mol, and the yield calculated as ring unit was calculated.

Yield of FRL (%)=(amount of FRL after reaction (mol)/amount of charged saccharide (xylan) (mol))×100

Example 1

<Production of Crude Furfural>

To a micro autoclave of 100 mL, 9.0 g of bagasse (having a weight average diameter of from 1 mm to 3 mm), 49.2 g of desalted water as a reaction solvent, and 1.8 g of lactic acid as a catalyst were charged; the container was sealed; and thereafter the internal space was replaced with nitrogen. The content was heated to a temperature of 170° C. with stirring, and the reaction was carried out by heating and stirring at 170° C. and 1.0 MPaG for 180 minutes.

After the reaction, with maintaining stirring, the reaction solution was allowed to be cooled to room temperature, and the whole amount of the reaction solution in the autoclave was recovered, so as to obtain crude furfural.

The concentration of FRL in the crude furfural was 1.2% by weight, and the yield of FRL was 36%.

As for this crude furfural, the type and concentration of the organic acids contained in the above method were determined, and the organic acids were formic acid, acetic acid and lactic acid. The concentrations of the organic acids were shown in Table 1 (Example 1).

<Two-Layer Separation of Crude Furfural>

To a glass vial of 9 mL, 2 g of the above crude furfural was charged; 2 g of tetralin was added thereto; the temperature was raised to 95° C.; and the mixture was stirred for 10 minutes. The solution was maintained at a temperature of 95° C. for 15 minutes of standing and then separated into two layers. The concentration of the furfural was measured by the GC analysis for each of the organic layer and the aqueous layer obtained from the two-layer separation, and then the distribution ratio of furfural (FRL) was calculated. In addition, the concentration of the organic solvent in the aqueous layer was measured by the GC analysis as well. The results were shown in Table 1.

Example 2

The two-layer separation was carried out in the similar manner as in Example 1, except that the temperature condition in two-layer separation was 100° C. The results were shown in Table 1.

Example 3

The two-layer separation was carried out in the similar manner as in Example 1, except that the temperature condition in two-layer separation was 120° C. The results were shown in Table 1.

Example 4

The two-layer separation was carried out in the similar manner as in Example 1, except that 2 g of 1-methylnaphthalene was added instead of tetralin. The results were shown in Table 1.

Comparative Example 1

The two-layer separation was carried out in the similar manner as in Example 1, except that the temperature condition in two-layer separation was 40° C. The results were shown in Table 1.

Comparative Example 2

The two-layer separation was carried out in the similar manner as in Example 1, except that the temperature condition in two-layer separation was 80° C. The results were shown in Table 1.

Comparative Example 3

The two-layer separation was carried out in the similar manner as in Example 1, except that the temperature condition in two-layer separation was 160° C. The results were shown in Table 1.

Comparative Example 4

The two-layer separation was carried out in the similar manner as in Example 3, except that 2 g of butylbenzene was added instead of tetralin. The results were shown in Table 1.

aqueous layer was also increased. Also in Comparative Example 4 (butylbenzene: 0.86 g/cm$^3$), in which the density at normal temperature (25° C.) and under atmospheric pressure (100 kPa) was lower than 0.90 g/cm$^3$ and a solvent other than the solvents specified in the present invention was used, the distribution ratio of furfural to the organic layer side was remarkably reduced, and the loss in organic solvent to the aqueous layer was also increased.

Therefore, it is known that at two-layer separation of the crude furfural, as in the present invention, when an aromatic hydrocarbon solvent having a density at 25° C. and under atmospheric pressure of from 0.90 g/cm$^3$ to 1.1 g/cm$^3$ is selectively used, the extraction efficiency of the furfural is enhanced in a specific high temperature range of higher than 90° C. and lower than 150° C.

While the present invention has been described in detail and with reference to specific embodiments, it will be apparent to those skilled in the art that various changes and modifications can be made without departing from the spirit and scope of the invention. This application is based on Japanese Patent Application (JP2016-074337) filed on Apr. 1, 2016, the contents of which are incorporated herein by reference.

The invention claimed is:

1. A method for producing furfural and extracting the produced furfural, comprising:
   reacting a non-edible biomass resource with a catalyst in a solvent, thereby obtaining a sugar solution comprising a monosaccharide having 5 carbon atoms, a polysaccharide containing the monosaccharide as a constituent component, or both;

TABLE 1

| | Concentration of organic acid in crude furfural (% by weight) | | | | | Temperature of | Distribution ratio of | Concentration of organic |
| --- | --- | --- | --- | --- | --- | --- | --- | --- |
| | Formic acid | Acetic acid | Lactic acid | Total | Solvent | two-layer separation (° C.) | FRL in organic layer (%) | solvent in aqueous layer (% by weight) |
| Example 1 | 0.2 | 0.6 | 3 | 3.8 | Tetralin | 95 | 75 | 0.15 |
| Example 2 | 0.2 | 0.7 | 3 | 3.9 | Tetralin | 100 | 72 | 0.07 |
| Example 3 | 0.2 | 0.6 | 3 | 3.8 | Tetralin | 120 | 70 | 0.03 |
| Example 4 | 0.2 | 0.6 | 3 | 3.8 | 1-methylnaphthalene | 95 | 82 | 0.10 |
| Comparative Example 1 | 0.2 | 0.7 | 3 | 3.9 | Tetralin | 40 | 67 | 3.40 |
| Comparative Example 2 | 0.2 | 0.7 | 3 | 3.9 | Tetralin | 80 | 72 | 0.81 |
| Comparative Example 3 | 0.2 | 0.6 | 3 | 3.8 | Tetralin | 160 | 56 | 0.32 |
| Comparative Example 4 | 0.2 | 0.6 | 3 | 3.8 | Butylbenzene | 120 | 61 | 0.87 |

From Table 1, the followings are seen.

In Examples 1 to 4, in which the aromatic hydrocarbon solvent specified in the present invention is used and the temperature in the two-layer separation is within the range specified in the present invention, the furfural can be extracted and separated in a high distribution ratio of FRL at the organic layer side, and the concentration of the organic solvent in the aqueous layer is also low.

In Comparative Example 1 (40° C.) and Comparative Example 2 (80° C.), in which the temperature in the two-layer separation was lower than 90° C., the loss in organic solvent to the aqueous layer was remarkably increased. In Comparative Example 3 (160° C.), in which the temperature in the two-layer separation was higher than 150° C., the distribution ratio of furfural to the organic layer side was remarkably reduced, and the loss in organic solvent to the converting the monosaccharide and/or the polysaccharide into furfural by a dehydration reaction, thereby obtaining a reaction solution containing the furfural; and separating the reaction solution into an organic layer and an aqueous layer at a temperature higher than 90° C. and lower than 150° C., such that the organic layer comprises the furfural and an aromatic hydrocarbon solvent, wherein the aromatic hydrocarbon solvent comprises at least one selected from the group consisting of tetralin and 1-methylnaphthalene.

2. The method according to claim 1, wherein the reaction solution comprises an organic acid in an amount of from 0.1% by weight to 40% by weight.

3. The method according to claim 1, further comprising:
after the converting and prior to the separating, controlling a concentration of an organic acid in the reaction solution to be from 0.1% by weight to 40% by weight.

4. The method according to claim 1, wherein the reaction solution comprises acetic acid in an amount of from 0.2% by weight to 2% by weight.

5. The method according to claim 1, wherein the method is carried out such that the furfural is continuously produced.

6. The method according to claim 1, wherein the non-edible biomass resource comprises bagasse and the aromatic hydrocarbon solvent comprises tetralin.

7. The method according to claim 1, wherein the aromatic hydrocarbon solvent comprises 1-methylnaphthalene.

8. The method according to claim 1, wherein the aromatic hydrocarbon solvent comprises tetralin.

9. The method according to claim 1, wherein the solvent used in the reacting comprises the aromatic hydrocarbon solvent.

10. The method according to claim 1, further comprising:
after the converting and prior to the separating, adding the aromatic hydrocarbon solvent to the reaction solution.

11. The method according to claim 1, wherein the separating is performed such that the aqueous layer comprises 0.15% by weight or less of an organic solvent.

12. The method according to claim 1, wherein the separating is performed such that the organic layer comprises 70% by weight or more of the furfural contained in the reaction solution subjected to the separating and that the aqueous layer comprises 0.15% by weight or less of an organic solvent.

13. The method according to claim 1, wherein the separating is performed at a temperature of from 95° C. to 120° C.

14. The method according to claim 13, wherein the separating is performed such that the organic layer comprises 70% by weight or more of the furfural contained in the reaction solution subjected to the separating and that the aqueous layer comprises 0.15% by weight or less of an organic solvent.

* * * * *